United States Patent
Babcock et al.

(10) Patent No.: US 9,027,388 B2
(45) Date of Patent: May 12, 2015

(54) METHOD AND APPARATUS FOR MEASURING PARTICLE CHARACTERISTICS THROUGH MASS DETECTION

(75) Inventors: Kenneth Babcock, Santa Barbara, CA (US); Thomas Burg, Cambridge, MA (US); Michel Godin, Beaconsfield (CA); Scott Manalis, Cambridge, MA (US)

(73) Assignees: Affinity Biosensors, LLC, Santa Barbara, CA (US); Massachusetts Institute of Technology, Cambridge, MA (US)

( * ) Notice: Subject to any disclaimer, the term of this patent is extended or adjusted under 35 U.S.C. 154(b) by 88 days.

(21) Appl. No.: 13/310,776

(22) Filed: Dec. 4, 2011

(65) Prior Publication Data

US 2014/0051107 A1    Feb. 20, 2014

Related U.S. Application Data

(63) Continuation of application No. 12/087,495, filed as application No. PCT/US2007/081045 on Oct. 11, 2007, now Pat. No. 8,087,284.

(60) Provisional application No. 60/850,776, filed on Oct. 11, 2006.

(51) Int. Cl.
  *G01N 15/00*  (2006.01)
  *G01N 5/00*   (2006.01)
  *G01N 9/00*   (2006.01)
  *G01N 15/10*  (2006.01)
  *G01N 15/02*  (2006.01)

(52) U.S. Cl.
  CPC .......... *G01N 15/00* (2013.01); *G01N 5/00* (2013.01); *G01N 9/002* (2013.01); *G01N 15/10* (2013.01); *G01N 15/1012* (2013.01); *G01N 2015/003* (2013.01); *G01N 2015/1043* (2013.01); *G01N 2015/1087* (2013.01); *G01N 15/0255* (2013.01)

(58) Field of Classification Search
  CPC ..................................................... G01N 15/00
  See application file for complete search history.

(56) References Cited

U.S. PATENT DOCUMENTS

2004/0038426 A1*  2/2004  Manalis ................. 436/514

\* cited by examiner

*Primary Examiner* — Hezron E Williams
*Assistant Examiner* — Mark A Shabman
(74) *Attorney, Agent, or Firm* — Mark Rodgers

(57) ABSTRACT

Method for measuring a target particle property. A suspended microchannel resonator is calibrated to determine the relationship between a detected mass and a resonance frequency shift of the resonator. The target particle is suspended in a fluid and introduced into the resonator, and the resonator frequency shift due to the particle is measured. Target particle mass is calculated from the resonator frequency shift, the target particle density, and the fluid density. A target particle property such as size or volume is determined from the calculated target particle mass.

7 Claims, 4 Drawing Sheets

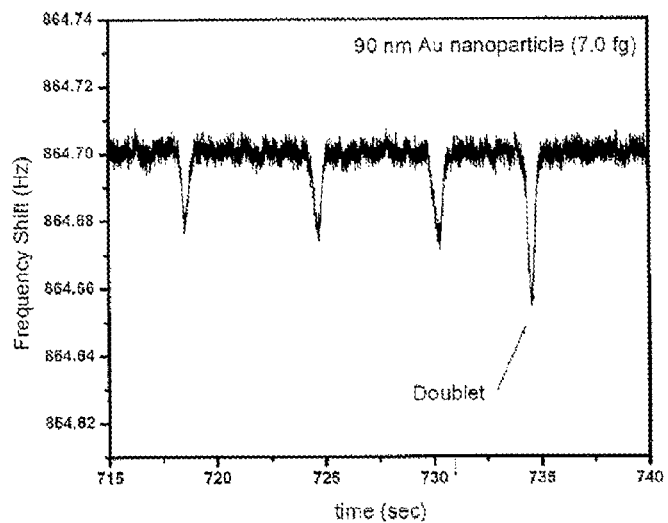
Figure 6
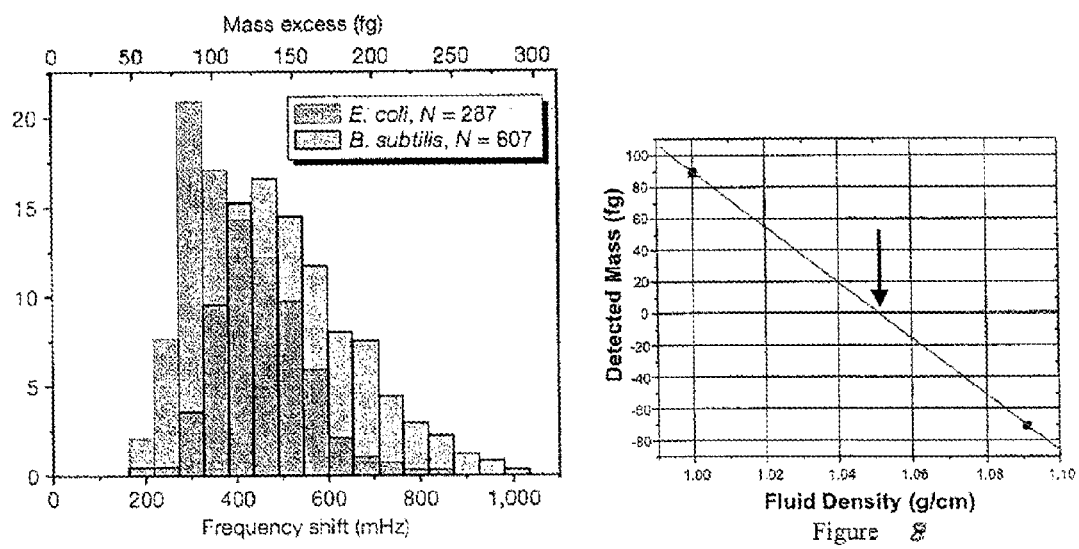
Figure 7
Figure 8

METHOD AND APPARATUS FOR MEASURING PARTICLE CHARACTERISTICS THROUGH MASS DETECTION

This application is a continuation of U.S. application Ser. No. 12/087,495, filed Jul. 8, 2008, which claims priority to PCT/US2007/081045, which in turn claims priority to provisional application Ser. No. 60/850,776 filed Oct. 11, 2006.

BACKGROUND OF THE INVENTION

This invention relates to method and apparatus for measuring a property such as mass, size or density of target particles, and more particularly to such a method using a suspended microchannel resonator.

Precision measurements of nanometer- and micrometer-scale particles have wide application in pharmaceuticals/drug delivery, paints and coatings, foods, and other major industries and fields of research. This need is growing due to the expanding use of particulate engineering across these industries, to emerging nano- and micro-particle manufacturing techniques, and to recent regulations governing quality control in the pharmaceutical industry.

The most widely used particle-sizing technology is light scattering [Jillavenkatesa, 2001]. The names in brackets refer to the attached references, the contents of which are incorporated herein by reference. Light scattering is a mature technology that uses laser light passed onto or through a sample containing the target particles. In one form of light scattering known as laser diffraction, a spatial intensity pattern of the light diffracted by the particles is recorded. In another form, known as dynamic light scattering, the time dependence of scattered light intensity is recorded. The distribution of particle sizes is then inferred using various theoretical models of light diffraction or particle movement due to Brownian motion. Light scattering can be used to characterize particles whose sizes range from several hundred microns down to 1 nanometer or even below. In the majority of applications, particles are suspended in a fluid that carries them through the instrument. Light scattering is employed in a wide range of commercially available instruments from Beckman-Coulter, Malvern, Horiba, Shimadzu, and many other manufacturers.

Light scattering suffers from certain limitations. For example, when using laser diffraction, determining particle size accurately can be problematic for some applications due to subtleties in the light scattering models. For a wide class of particles, a priori knowledge of the optical indices of refraction of the particles and the carrying medium is required, and errors in the index values result in errors in estimated size [Keck 2000, Jillavenkatesa 2001]. For example, many paint pigments are made up of particles whose optical properties and shape affect their bulk color, and index parameters must be measured prior to size measurement [Ley]. Other examples include artifacts introduced by irregularly shaped particles that can cause errors when attempting to determine the particle volume and the "equivalent" spherical radius. Laser diffraction is also known to be problematic when measuring widely polydisperse and multimodal samples, for which measurements may miss entire peaks in the distribution of particle sizes, or indicate spurious peaks in the size distribution [Keck 2000, Driscoll 2001]. In the case of dynamic light scattering (DLS, also referred to as photon-photon correlation), the instruments detect a laser speckle pattern in the diffracted light, and monitor the pattern's changes in time that are caused by the Brownian motion of the particles. The autocorrelation function of the time dependence of this intensity is interpreted with the help of a theoretical model to infer the particle sizes. The resolution of DLS, i.e., its ability to distinguish among particles closely spaced in size, is fairly low, and this method is not well suited to providing the details of a complex distribution of particle sizes.

In order to reduce error and to increase resolution, when measuring polydisperse samples with light scattering, the samples are often "fractionated", i.e., the particles are sorted according to size, prior to measurement by light scattering. The sub-samples of different size "bins" are then measured successively with the light scattering instrument, and the overall distribution is built up. A number of fractionation techniques can be employed (settling, centrifuge, asymmetric field flow). The added sample preparation, the need to run several sub-samples, and additional equipment all add time and expense to the overall measurement.

In the case of laser diffraction, obtaining high resolution and wide dynamic range in the size measurement requires a large number of detectors to capture light scattered at various angles. For example, one high-end light scattering instrument uses 126 detectors (Beckman Coulter LS 230 Laser Diffraction Particle Size Analyzer). Other instruments use multiple laser light sources and polarizing optics (Beckman Coulter LS 13 320 Multi-Wavelength Particle Size Analyzer). The refined optics needed in these instruments results in high cost, with some instrument prices greater than $50,000. And, these optics must be precisely aligned and carefully calibrated.

Light scattering instruments require a large number of particles in the laser beam to create good statistics for the measurement, and typically use a relatively large amount of target sample (typically several milliliters of high-concentration particles for the case of fluid suspension). This can be a burden for applications where the target material is expensive, rare, or difficult to handle. In addition, light scattering is limited to providing a measure of particle size. In many applications, it would be desirable to measure other particle properties, such as mass and density, that cannot be determined with optical methods.

Other techniques are also used for particle size analysis, each having their own tradeoffs and limitations [Jillavenkatesa 2001].

Measurement of particulate properties is important for organic targets such as cells and bacteria. The Coulter counter, which uses an electrozone measurement principle, is a standard technique for measuring cell volume. The resolution of this approach is typically limited to sizes above a micron. Measurements of cell mass and density have been correlated with disease and other physiological states, for example, in the case of malaria [Kramer 1982], but the measurement techniques for these quantities remain laborious. In sum, there is a significant need for improved methods of measuring particulate characteristics including size, mass, volume, and density, at high resolution, precision, and accuracy, for both inorganic and organic targets.

SUMMARY OF THE INVENTION

In one aspect, the method according to the invention for measuring a target particle property includes calibrating a suspended microchannel resonator to determine the relationship between a change in mass of the resonator caused by a change in the contents of its microchannel, and a shift in resonance frequency of the resonator. A target particle is introduced into the resonator, and the resonator frequency shift is measured. The particle is typically suspended in a fluid, and the particle is introduced by flowing the fluid through the resonator. The target particle mass is calculated from the resonance frequency shift caused by the presence of the particle, the fluid density, and the target particle density. The calculated target particle mass enables a determination of additional target particle properties such as size or volume. In yet another aspect, the invention is a method for measuring density of a target particle including introducing a target particle in a first fluid having a first density into a suspended microchannel resonator and measuring a frequency shift. The target particle is then introduced in a second fluid having a second density different from the first density into the resonator, and the resonance frequency shift is again measured. A determination is then made of the fluid density that would produce no resonator frequency shift, this fluid density being the target particle density. The density measurement can also be used to determine the mean density of a population of particles.

In yet another aspect, the invention is a method for measuring fluid density comprising calibrating a suspended microchannel resonator to determine the relationship between a particle mass and a frequency shift of the resonator. A target fluid is seeded with particles of a known mass. This seeded fluid flows through the resonator and the resonance frequency shift is measured from which fluid density may be determined.

BRIEF DESCRIPTION OF THE DRAWINGS

FIG. 6 is a graph of resonance frequency shift as a function of time for 90 nm gold particles.

FIG. 7 is a graph showing the distribution of detected mass for populations of *E. coli* and *B. subtilis* bacteria.

FIG. 8 is a graph of detected mass as a function of fluid density.

FIG. 11a is a schematic illustration of an SMR sensor containing multiple particles.

FIG. 11b is a graph showing the SMR response as multiple particles pass through.

DESCRIPTION OF THE PREFERRED EMBODIMENT

Figure 1:
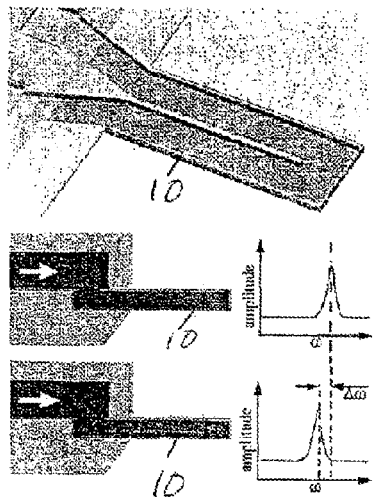
FIG. 1 is a schematic illustration of a suspended microchannel resonator.

Here we propose a new method for measuring the mass, size, and density of particles whose sizes range from the nanometer scale to many microns. The method employs a recently-introduced mass sensor known as the suspended microchannel resonator (SMR)[Burg and Manalis 2003; Burg 2007]. The SMR uses a fluidic microchannel embedded in a resonant structure, one type being in the form of a cantilever 10 (FIG. 1). The top diagram in F*ig*.1 is cutaway to show the microchannel interior, but in fact the channel is fully enclosed. Target particles are carried through the sensor in a fluid, and their contribution to the total mass within the sensor causes the resonance frequency of the sensor to change in relation to the particle mass. By using microfabrication techniques, SMR sensors can be fabricated with mass resolution of less than 1 femtogram ($10^{-15}$ g). This resolution is sufficient to detect and measure the mass of individual particles in the range of several nanometers up to many microns in size. SMR sensors can be made in a cantilever form 10 as in FIG. 1, or alternatively in a torsional geometry, or in a straight geometry with the microchannel suspended at its ends. SMR sensors have exceptional linearity, and dynamic range spanning many orders of magnitude [Burg 2007].

Measuring shifts in SMR resonance frequency can be achieved by a number of different methods. In one method, the resonator is driven into oscillation by applying an oscillating voltage to an electrode near the resonator. By using a gain-controlled oscillator circuit in which the resonator is the frequency-determining element, the resonator will continually oscillate at its resonant frequency. As the SMR's total mass changes, its shift in resonance frequency can be measured by simply monitoring the oscillation frequency [Burg 2007]. Alternatively, the resonator could be driven at a constant frequency, and its phase measured relative to the drive signal. In this case shifts in measured phase can be related to the shift in resonance frequency. Similarly, a phase locked loop circuit can be used. The methods of particle measurement described herein are understood to be enabled by any method that monitors a shift in resonance frequency of the SMR sensor.

Using microfabricated resonant mass sensors to measure fluid density is known in the literature [Enoksson 1996, Corman 2000]. However, the use of resonant mass sensors to measure properties of individual particles and other entities suspended in fluid has not been identified previously in the densitometry art, and constitutes a novel aspect of the present invention. The prior embodiments of fluid density sensors had insufficient resolution to detect and measure individual particles at the micron and submicron scale. The miniaturization and improvement of several orders of magnitude in mass resolution as demonstrated by the inventors constitutes another aspect of novelty and enables mass sensing to address important applications in particle measurement.

SMR sensors, which do not require optics, can be manufactured using MEMS techniques to be robust and cost-effective, costing $10-100 per sensor "chip". The SMR platform, and the particle characterization methods described here, can compose instruments that are much less expensive than existing light-scattering instruments.

Figure 2:
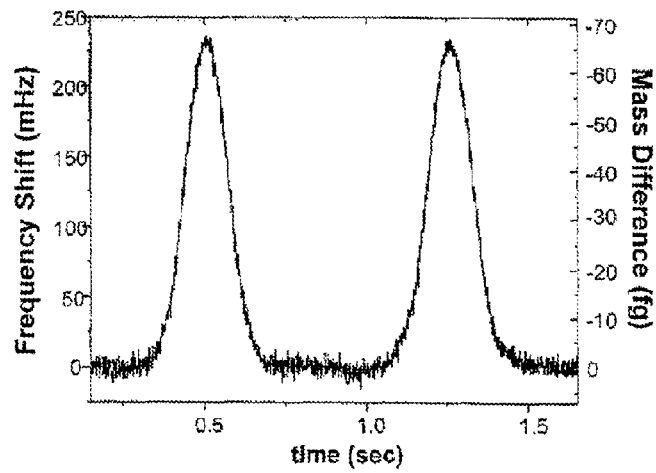
FIG. 2 is a graph of resonance frequency shift and mass difference as a function of time.

FIG. 2 shows the SMR signal due to individual polystyrene spheres suspended in a glycerol/water mixture as they pass through the SMR sensor. The peaks in the signal occur when the particles reach the apex of the sensor, where they have the biggest effect on the resonator's effective mass, and hence resonance frequency shift. Note that the key measurement is the resonance frequency shift caused by the particle, relative to the baseline associated with the resonator filled with pure fluid. The SMR sensors can be calibrated using particles of known mass and density to determine the relation between particle mass and the frequency shift at the signal peaks. Alternatively, SMR sensors can be calibrated by comparing the resonant frequency with fluids of known density, or comparing the resonant frequency between a dry state and with a fluid inside. Calibrating for particle measurements then requires a simple geometrical factor relating the effects of bulk mass distributed throughout the sensor (as with a fluid) vs. a particle localized at the end of the sensor. FIG. 2 shows the detected mass difference in the case of the polystyrene spheres for this calibrated sensor.

The SMR sensor detects the mass difference caused by the particle presence vs. the case of no particle, i.e., it detects the excess mass over that of the fluid displaced by the particle volume: detected mass=particle mass−(particle_volume×fluid_density), where particle_density denotes the material density of the particle (typically [g/cc]). Using the relation particle_mass=particle_density×particle_volume, we can determine the actual particle mass as particle_mass=detected_mass/(1−fluid_density/particle_density). These relations capture an analog of Archimedes's law, wherein we are interested in the effect of mass on a resonator rather than in gravity-induced buoyancy forces.

In the case of FIG. 2, the detected mass difference is −69.6 fg. For that data a glycerol/water mixture of density 1.091 g/cc was used. Polystyrene has a density of 1.05 g/cc. Using the above relation we find the actual particle mass to be $(-69.6)/(1-1.091/1.05)$ fg=1.78 pg $(1.78 \times 10^{-12}$ g). Note that when the fluid is denser than the particle, the particle is buoyant and the net detected mass change is negative.

From the measured particle mass, the particle volume can be determined directly as particle_volume=particle_mass/particle_density. Corresponding linear sizes can also be determined by using relations between volume and size for simple shapes. For example, assuming a spherical shape the diameter D can be determined by using the relation: particle_volume=$(4/3) \times PI \times (D/2)^3$. For the polystyrene spheres in FIG. 2 we determine the mean effective particle diameter to be D=1.49 microns, which is consistent with the particle manufacturer's specification for these particles. Linear particle dimensions of other assumed shapes (e.g., ellipsoids of known eccentricity, polygons, and many others) can be determined with a similar approach.

Figure 3:
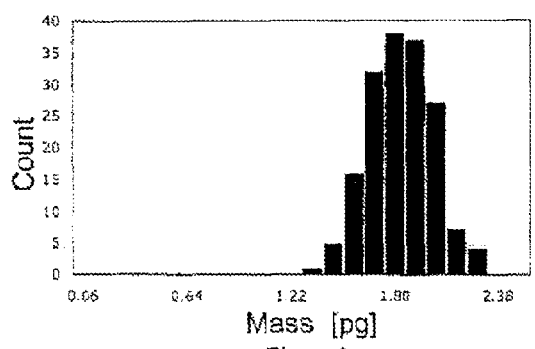
FIG. 3 is a graph showing the distribution of particle masses of polystyrene spheres.
Figure 4:
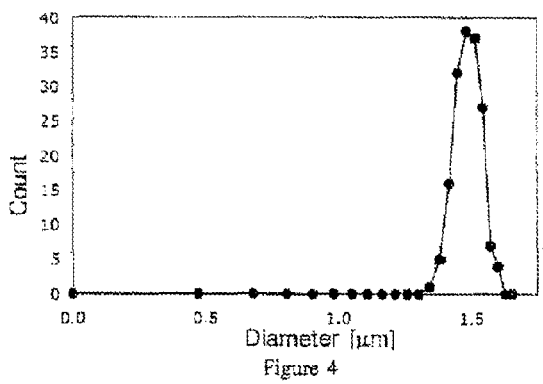
FIG. 4 is a graph showing the distribution of sizes for a monodisperse sample of polystyrene spheres in water.
Figure 5:
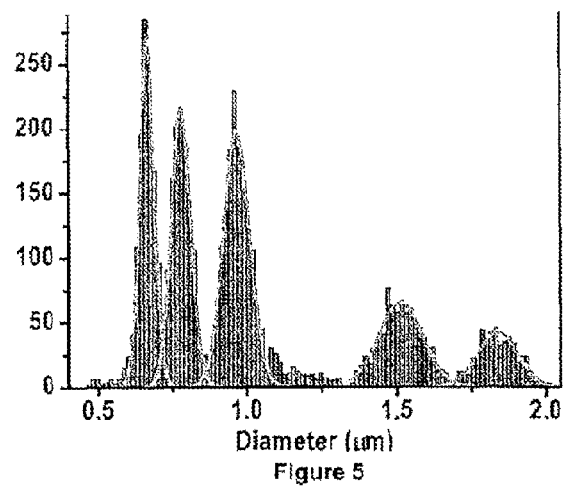
FIG. 5 is a graph showing the distribution of sizes for a sample made up of polystyrene spheres of five distinct sizes in water.

In summary, particle characteristics can be determined by the method of
1) calibrating the SMR to measure mass differences due to the presence of particles
2) measuring the mass differences due to the presence of a target particle
3) using this data plus the particle density and fluid density to determine the actual particle mass, and
4) determine the particle volume and particle size A complete distribution of masses and sizes for a population of particles can be determined by measuring a number of representative particles. FIG. 3 shows the distribution of particle masses for 167 polystyrene spheres. FIG. 4 shows the corresponding distribution of sizes, in this case the effective diameters, calculated from the mass data via the relations above. The polystyrene spheres were measured to have a mean mass of 1.79 pg with standard deviation ±0.30 pg, and mean size 1.49±0.02 microns, again consistent with manufacturer's specifications. Note that there is no ambiguity in determination of the mass and effective diameter of any individual particle, nor of the overall distribution, so long as the SMR sensor is calibrated and the fluid and particle densities are known. All characteristics of the distributions (mean size, variance, higher central moments, skew, kurtosis, etc.) can be determined precisely and accurately so long as measurements of a sufficiently large number of particles are made to give good statistics. This holds true for simple narrow, "monodisperse" distributions as well as broad or even "polydisperse" populations that may have a wide range of sizes. It also holds for multimodal distributions having more than one characteristic size, as illustrated in FIG. 5. In that example, polystyrene spheres of five distinct sizes were mixed in water, and measurements of 5,398 particles were made in a single run to produce the shown distribution. Because each particle is measured precisely and accurately, no sample pre-fractionation is required. And, measurements of the particle mass are not sensitive to variations in shape.

For the measurements in FIGS. 4 and 5, we assume that only one particle is present in the resonator at a given time, and the particle exits the sensor before the next one enters. This assumption is met by suspending the particles in the fluid such that their volume concentration is less than (1/(resonator volume)), which for the SMR sensors in [Burg 2007] is $<\sim 10^8$ particles/cc. As a practical matter, "coincidences", in which more than one particle do occupy the sensor simultaneously, may occur occasionally, but will have minimal statistical effect on the distributions so long as they are rare. Conversely, by working with a dilute sample, the SMR can be used to detect particle aggregates, indicated by large resonance frequency shifts. For example, in the case of a monodisperse particle population, aggregation will be revealed as measured masses which are multiples of the single particle mass, i.e., monomers, dimers (doublets), trimers (triplets), and so on. FIG. 6 shows measurements of three monomers and one dimer of 90 nm gold particles.

The methods described here assume target particles pass through and exit the sensor. While most particles behave this way, in some cases it is possible to detect the presence of particles when they stick to the interior walls. The resulting SMR signal shows a step in the resonance frequency shift. For a given particle mass, the size of the step depends on the location of the particle, with the largest steps occurring when the particle lodges at the end of the resonator. If the particle location could be known, the particle mass and size could be determined using the methods described here. Such an approach may be useful when detecting or measuring a certain sub-population of particles in a complex background. For example, immunoassay methods using antibodies could selectively capture certain particles and determine their mass or concentration. Conversely, using coatings such as polyethylene glycol flowed through the sensor in advance, SMR sensors can easily be prepared so as to prevent sticking of any particles to the interior walls.

At demonstrated mass resolutions of ~1 fg, SMR is capable of measuring particles that are sub-micron in size. FIG. 6 shows SMR measurements of gold particles of diameter 90 nm (mass 7 fg), and the same sensors can detect gold particles as small as 52 nm (mass 1 fg). Particles with density closer to a typical carrier fluid such as water produce less SMR signal for a given actual mass than a dense material such as gold. Again, this is because the mass difference detected by the SMR will decrease as the fluid and particle densities become closer in magnitude. For example, polystyrene has a density of 1.05 g/cc vs. 1.0 g/cc for pure water. Thus, with an SMR detection limit of 1 fg, the smallest detectable polystyrene sphere would have mass=minimum detected mass/(1−fluid density/particle density)=(1 fg)/(1−1.0/1.05)=21 fg, with a corresponding diameter of 370 nm. Conversely, using a fluid with density that differs more from that of the particle can improve actual mass resolution. For example, using sugar water of density 1.4 g/cc would reduce the minimum detectable polystyrene particle size to ~195 nm, and even denser fluids, such as CsCl solutions (density up to 1.7 g/cc), can be used. Less dense fluids such alcohols (e.g., ethanol, density 0.789 g/cc) can be used to enhance SMR response to some particles, e.g., silica (density~1.8 g/cc). In addition, longer measurement times for each particle, and successive generations of SMR sensors, will likely improve mass resolution. One could achieve longer measurement times without reducing throughput significantly by temporarily reducing the fluid flow to near-zero or zero while the particle is at the apex. It may be expected that the mass- and size-measurement method described here could allow sizing of particles down to the nanometer scale.

These methods can also be used to measure sizes of larger particles, limited only by the fluidic channel, whose bore must be sufficiently large to allow the particles to pass through. Current SMR devices can accommodate particles of several microns, and devices accommodating particles that are tens or hundreds of microns or even larger in size would be straightforward to manufacture.

These methods can also be used to characterize emulsions in which immiscible droplets of one fluid are suspended in a matrix of a different fluid. Droplet mass, volume, and size can be determined as above provided the densities of the droplet and carrier fluids differ at least slightly from one another and are known.

All of the above methods can be applied to measurement of certain organic samples, including cells, bacteria, and organelles [Burg 2007]. FIG. 7 shows the frequency shift and detected mass distributions for cultures of live *E. coli* and *B. subtilis* bacteria suspended in phosphate buffered saline solution. Details of the bacteria mass distribution such as width and asymmetry provide insight into bacterial growth and division processes [Akerlund 1995]. For the methods and embodiments described here, measurement of particles should be understood to apply equally well to cells, organelles, bacteria, spores, platelets and other blood components, droplets in emulsions, and any other matter of particulate form suspended in a fluid.

While the above methods focus on measurement of properties of individual particles, the suspended microchannel resonator can also be employed in the simpler task of detecting particles and measuring their concentration (i.e., number/volume) in a fluid. Detection can be accomplished by simply monitoring the SMR signal for transient events indicative of particles passing through the sensor. Sensor calibration is not necessary in this case. Particle concentration can be determined by flowing the fluid at a known rate, and measuring the mean time interval between detection of particles. The particle concentration can then be determined as 1/(flow rate× mean time interval).

The above particle sizing method requires knowledge of the particle density in order to determine particle mass and size. In many practical applications this information will be available. If desired, however, SMR can be used to measure the density or specific gravity of the particles. In one method the particles are measured twice, in fluids of two different densities. As shown in FIG. 8, the SMR responses for the two fluids are interpolated (or extrapolated) to determine the fluid density that would yield no SMR response, thereby giving the particle density. In FIG. 8 the measured particle density is 1.051 g/cc, in good agreement with polystyrene density of 1.050 g/cc. As a practical matter, the average SMR signal for many particles can be determined for each of the fluid densities (as was the case for FIG. 8). These average values can then be used to determine the mean density for the entire particle population. Note that this method of determining particle density does not require that the SMR sensor be calibrated to relate shifts in resonance frequency to detected mass.

Figure 9:
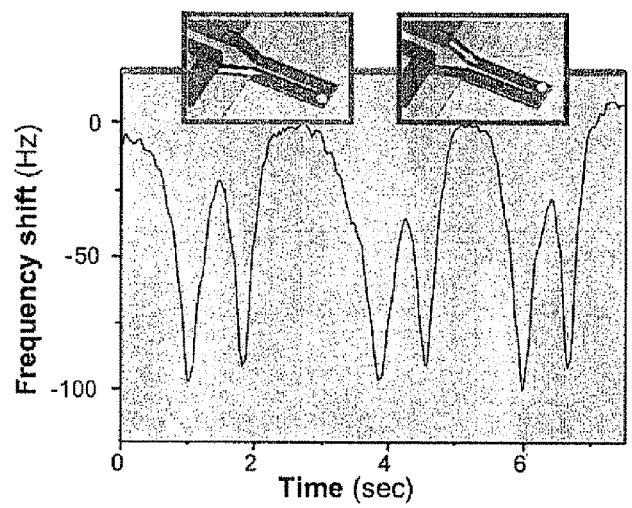
FIG. 9 is a graph showing the resonance frequency response as a bacterium is carried through the SMR alternately by two fluids of differing density.

The same method can be used to measure the density of a single particle provided the particle is identified or manipulated, and measured successively in fluids of different densities. In one method, a particle could be trapped or otherwise held at the apex of the sensor during measurement. The fluid could then be swept past the particle and the fluid density changed. The SMR response could then be monitored and the particle density determined as in FIG. 8. Trapping could be accomplished by, for example, applying a local electric field at the sensor apex, which would attract conducting or dielectric particles; or (for certain particles) by applying magnetic fields. As mentioned previously, such trapping would also allow extended measurements and more precise determinations of particle mass. FIG. 9 illustrates this method by repeatedly carrying a single *E. coli* bacterium back and forth through the apex of the SMR sensor. The bacterium is carried alternately by a fluid having a first density flowing in one direction, and then by a different fluid having a second density in the reverse direction. The peaks in the SMR response show different characteristic magnitudes for the two fluids. These peak values can be extrapolated to determine the particle density as in the previously described method.

Figure 10:
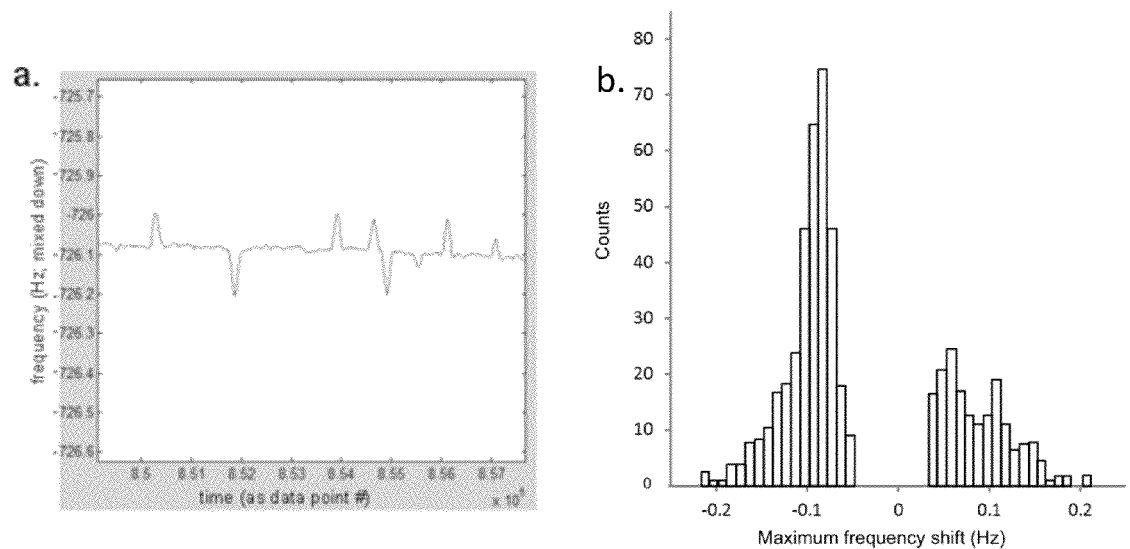
FIG. 10 is a graph showing distinct mass signatures for two bacteria types.

Measurements of particle mass and density may be used to distinguish among different particle types in a mixture, or to identify types of particles. FIG. 7 shows that a mass measurement of a mixture of two particle populations may overlap considerably, and so the measurement of the mass of a single particle may not yield a signal indicative of particle type. A method that does, in some cases, allow distinguishing among particle types exploits the fact that the SMR resonance frequency shift caused by a particle depends on the density of the suspending fluid. This method is illustrated in FIG. 10a, in which a mixture of *B. subtilis* bacteria and *E. coli* STET bacteria was passed through an SMR sensor. The positive peaks in the SMR response are caused by the gram-negative *B. subtilis* bacteria, while the negative peaks are caused by the gram-positive *E. coli*. bacteria. (By running the species independently it was verified that all bacteria within a population gave the same sign in SMR response.) The response in FIG. 10a is achieved by choosing a fluid medium whose density is between the mean density of the *E. coli* and that of the *B. subtilis*; in FIG. 10 the fluid was a mixture of PBS and 27.5% histodenz (Sigma Aldrich). The corresponding distribution of detected masses is shown in FIG. 10b, illustrating the separation of the two populations into separate groups distinguished by the sign of the SMR resonance frequency shift. The resulting data could be used to determine the presence and concentration of the two populations in a sample. This method could be extended to more than two particle types by measuring the sample in multiple fluids of different densities, and carefully analyzing the resulting data.

The ability to detect particles can also be used as an alternative method for measuring fluid density as follows:
1) calibrate an SMR sensor to measure particle mass per methods previously described
2) seed target fluid with particles of known mass and density
3) flow seeded fluid through SMR sensor and measure the "detected" particle mass
4) invert previous expression to determine fluid density: fluid density=particle density×(1−(detected mass/particle mass)).

SMR sensors require significantly less sample volume than typical light scattering instruments. Current SMR devices have sensor volume of ~10 picoliters [Burg 2007], much smaller than the flow cell volumes of typical light scattering machines (typically in the range of several milliliters). SMR measurements are typically made with only one particle present in the sensor at a time. An estimate of minimum required sample is given by (sensor volume)×(number particles to be measured). Assuming 500 particles must be measured to determine an accurate distribution, we estimate-5-10 mL as the minimum required sample size. Even with suboptimal fluid handling and sparser samples, it is likely that SMR-based detection will require many orders of magnitude less sample than typical light scattering instruments, a valuable attribute for rare and expensive targets.

The throughput of an SMR measurement of a distribution of particles is determined by the time required to measure an individual particle and the number of particles to be measured. Current SMR systems require that a particle spend ~0.1-1 second in the sensor to afford adequate resolution for the smallest particles (near 1 fg in mass). To measure a population of 500 particles would then require ~1-10 minutes. SMR throughput could be increased by increasing SMR sensitivity, thus allowing faster per-particle measurements and higher flow rates while maintaining adequate resolution. Alternatively, arrays of SMR sensors could be operated in parallel. Since each sensor does not need individual fluidic addressing, it should be possible to operate 100-1000 resonators on a single sensor chip, allowing measurements of particle populations in less than a minute.

The above inventions and embodiments emphasize measurements of one particle, or one aggregate of particles, at a time. Similar methods can also be applied to cases in which multiple particles occupy the SMR sensor at a given time, as shown in FIG. 11(a). This might be the case, for example, if the SMR sensor volume is made sufficiently large, or the particle concentration is sufficiently high. The multiple-particle configuration is amenable to measuring mean properties of a particle population, such as mean particle mass or mean particle density. In the case of a large number of particles present in the SMR, the detected mass is distributed throughout the resonator volume, and the particles can be thought of as changing the bulk mass density in the SMR, that is, the density averaged throughout the SMR volume. As the particles pass through the resonator microchannel the SMR signal will appear as in the lower part of the graph in FIG. 11(b). Here the time averaged resonant frequency shift (dashed line in FIG. 11(b)) is proportional to the time average of the detected change in bulk mass density caused by the presence of the particles. A calibration factor relating the shift in resonance frequency of the SMR to changes in bulk mass density inside the sensor can be determined by observing the difference in resonance frequency for two pure fluids of know density. Once calibrated, the time averaged resonance frequency shift of the SMR will yield the time averaged bulk mass density change due to the multiple particles, which can then be related to mean particle properties as:

detected bulk_mass_density_change=mean_particle_concentration×mean_particle_volume×(mean_particle_density−fluid density)

where the units of (mean_particle_concentration) are [number/volume], and the bulk density change is measured relative to the case of pure fluid (upper, smooth portion of the curve in FIG. 11(b)). The small time variations in FIG. 11(b) are caused by fluctuations in the number of particles in the resonator volume and variations in their spatial distribution, both of which cause fluctuations in the detected bulk mass density. These fluctuations are analogous to the well-known phenomenon of electrical "Shot" noise associated with direct current flow. From the measured time-average detected mass density, and using the above relation, we can determine, for example:

the mean particle volume and mass, assuming the mean particle concentration and density, and fluid density, are known:
mean_particle_volume=(time_average_detected_mass_density_change)/(mean_particle_concentration*(mean_particle_density−fluid_density);
and mean_particle_mass=mean_particle_volume× mean_particle_density;
and mean_particle_size, calculated using geometrical relations between volume and linear size.

the fluid density, assuming the mean particle mass and concentration are known:
fluid_density=mean_particle_density×(1−(time_average_detected_bulk_mass_density_change)/(mean_particle_concentration×mean_particle_mass)).

the mean particle concentration, assuming the mean particle mass and mean particle density, and fluid density are known;
mean_particle_concentration=(time_average_detected_bulk_mass_density_change)/((mean_particle_mass)*(1−fluid_density/mean_particle_density)).

Figure 11:
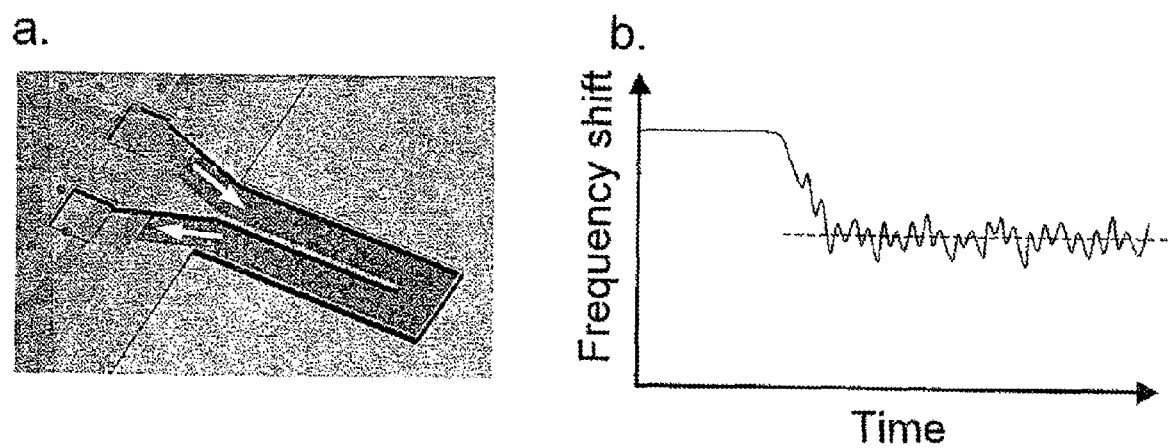

The multiple-particle configuration of FIG. 11 allows measurements of mean particle properties for a population even in cases where the individual particles have masses that are too small for an SMR sensor to detect, so long as a sufficient number of particles occupy the SMR sensor to create a measurable change in bulk mass density. It may also allow more rapid measurements of mean particle properties than sequential measurement of individual particles.

While FIG. 11(a) shows numerous particles inside the sensor, the above methods could be applied in cases in which several or a few particles occupy the sensor at once. In these cases the fluctuations illustrated in FIG. 11(b) would become relatively large, but sufficient time averaging will nonetheless allow the mean particle and/or fluid properties to be determined.

The multiple-particle configuration of FIG. 11 can also be used to determine the mean particle density of a particle population, even when the mean particle volume is not known. As in the single particle method shown in FIG. 8, the particle population is suspended in separate fluids of different densities, and the time average of the frequency shift caused by the particles is measured for each suspension. As in FIG. 8, the measurements are extrapolated (or interpolated) to determine the fluid density that would yield no SMR response. This density is equivalent to the mean particle density for the population. Note that this measurement does not require that the SMR sensor be calibrated to relate resonance frequency shifts to bulk mass density.

For many of the multi-particle measurements it is useful to know the mean particle concentration. For many samples this information is available from the details of the sample preparation. In cases where it is not known in advance, the number concentration could be determined by the time frequency of fluctuations shown in FIG. 11(b) and the fluid flow rate using the relation: mean particle concentration=fluctuation frequency/flow rate. This relation assumes each fluctuation in the signal corresponds to a single particle. This relation thus becomes more precise as the particle concentration decreases, or, alternatively, as the SMR sensor volume is decreased. Indeed, a second SMR sensor of small volume could be placed in series with a large multi-particle sensor and the sample passed through both. The smaller sensor will contain fewer particles at a given time than the larger sensor, allowing the fluctuations to be more easily resolved. The second sensor could be chosen to allow only a single particle to occupy it at once, allowing the particle concentration to be determined, and all of the single particle methods described in this text to be used in a confirmatory role.

As compared to the prior art densitometry and mass sensing art the SMR and methods disclosed herein allow for the first time direct measurements of the mass and density, and effective size, for individual particles of mass down to 1 fg and below, and in the size range of nanometer-micrometer and larger. With respect to existing particle sizing technologies such as light scattering, SMR and the methods disclosed herein afford direct measurements of individual particle mass, volume and size. The method reduces or eliminates artifacts due to irregularity in particle shape and variations or uncertainty in particle index or chemical make-up. There is no dependence on complex models to interpret SMR data. Further, the methods disclosed herein provide accurate distributions of entire populations of particles no matter how uniform or polydisperse, and without the need for pre-fractionation. The present invention also allows independent measurements of the material density of a particle population with the same instrument, and the identification of particle types by their mass and density signatures. The present invention can also be used to determine mean properties of a particle population including mean mass and mean mass density by measuring the time averaged response of an SMR sensor containing multiple particles. The present invention also results in consumption of much less sample than conventional instruments, in the nanoliter-microliter range. The invention also permits MEMS-based fabrication and more robust and cost effective instrumentation.

References

A. Jillavenkatesa, S. J. Dapkunas, and L. S. H. Lum, "Particle Size Characterization", NIST Special Publication 960-1, 2001.

T. P. Burg, M. Godin, S. M. Knudsen et al., "Weighing of biomolecules, single cells and single nanoparticles in fluid," Nature 446 (7139), 1066-1069 (2007).

M. Godin, A. K. Bryan, T. P. Burg, K. Babcock and S. R. Manalis, "Measuring the mass, density and size of particles and cells using a suspended microchannel resonator", accepted for publication in Applied Physics Letters.

C. M. Keck, "Cyclosporine Nanosuspensions", doctoral thesis, FU Berlin, June, 2006.

I. Ley, "A Colourful Tale—The Particle Size Analysis of Pigments", Beckman Coulter UK Ltd.

K. J. Kramer, S. C. Kan, and W. A. Siddiqui, "Concentration of *Plasmodium falciparum*-infected erythrocytes by density gradient centrifugation in Percoll," J Parasitol 68 (2), 336-337 (1982).

Burg and Manalis, "Suspended microchannel resonators for biomolecular detection," *Appl. Phys. Lett.* 83: 2698-2701 (2003).

P. Enoksson, G. Stemme, E. Stemme, "Silicon tube structures for a fluid-density sensor", Sensors and Actuators A 54 (1996) 558-562.

T. Corman, P. Enoksson, K. Noren and G. Stemme, "A low-pressure encapsulated resonant fluid density sensor with feedback control electronics", Meas. Sci. Technol. 11 (2000) 205-211.

D. F. Driscoll, F. Etzler, T. A. Barber, J. Nehne, W. Niemann, B. R. Bistrian, "Physiochemical assessments of parental lipid emulsions: light obscuration vs. laser diffraction", Int. J. Pharmaceutics 219 (2001) p. 21.

Akerlund, T., Nordstrom, K. & Bernander, R. Analysis of cell size and DNA content in exponentially growing and stationary-phase batch cultures of *Escherichia coli. J. Bacteriol.* 177, 6791-6797 (1995).

What is claimed is:

1. Method for measuring a property of a target particle comprising:
    calibrating a suspended microchannel resonator to determine the relationship between the resonance frequency of the resonator and the detected mass due to the presence of a particle inside the resonator using at least one of particles of known mass and density and fluids of known density;
    introducing a single target particle into the resonator along with a fluid at a particle/fluid volume concentration near or less than 1/(resonator volume) and measuring the shift in resonance frequency; and
    calculating a property of the single target particle from the shift in resonance frequency.

2. The method of claim 1 wherein the property is mass and mass is calculated by the equation particle mass = detected mass/(1 − fluid density/particle density).

3. The method of claim 1 wherein the property is volume and volume is calculated by the equation particle volume = detected mass/(fluid density − particle density).

4. Method of claim 1 wherein the property is diameter and diameter is determined by the relationship diameter=CubeRoot(6 ×detected mass/(Pi*(fluid density−particle density))).

5. The method of claim 1 wherein the property is linear size and linear size is determined using relations between volume and size for selected shapes.

6. Method of claim 1 wherein the target particles are droplets in an emulsion.

7. Method of claim 1 wherein the target particles are cells.

* * * * *